United States Patent
Shin et al.

(10) Patent No.: US 10,034,949 B2
(45) Date of Patent: Jul. 31, 2018

(54) POLYVALENT PNEUMOCOCCAL POLYSACCHARIDE-PROTEIN CONJUGATE COMPOSITION

(71) Applicant: SK CHEMICAL CO., LTD., Seongnam-si (KR)

(72) Inventors: Jin-Hwan Shin, Seoul (KR); Ji-Hye Yang, Seoul (KR); Dong-Soo Ham, Suwon-si (KR); Mahn-Hoon Park, Yongin-si (KR); Hun Kim, Suwon-si (KR); Myeong-Ju Noh, Seoul (KR); Su-Jin Park, Seongnam-si (KR); Seon-Young Yang, Incheon (KR)

(73) Assignee: SK CHEMICALS CO., LTD., Gyeonggi-Do (KR)

(*) Notice: Subject to any disclaimer, the term of this patent is extended or adjusted under 35 U.S.C. 154(b) by 0 days.

(21) Appl. No.: 14/409,865

(22) PCT Filed: Jun. 19, 2013

(86) PCT No.: PCT/KR2013/005392
§ 371 (c)(1),
(2) Date: Dec. 19, 2014

(87) PCT Pub. No.: WO2013/191459
PCT Pub. Date: Dec. 27, 2013

(65) Prior Publication Data
US 2015/0190520 A1 Jul. 9, 2015

(30) Foreign Application Priority Data

Jun. 20, 2012 (KR) .................. 10-2012-0065893

(51) Int. Cl.
*A61K 39/09* (2006.01)
*A61K 39/39* (2006.01)
*A61K 47/64* (2017.01)
*A61K 39/00* (2006.01)

(52) U.S. Cl.
CPC .......... *A61K 47/646* (2017.08); *A61K 39/092* (2013.01); *A61K 39/39* (2013.01); *A61K 47/6415* (2017.08); *A61K 2039/545* (2013.01); *A61K 2039/55505* (2013.01); *A61K 2039/6037* (2013.01); *A61K 2039/70* (2013.01)

(58) Field of Classification Search
CPC ........ A61K 39/092; A61K 2039/55505; A61K 2039/6037; A61K 39/385; A61K 2039/6031; A61K 2039/64; A61K 2039/70; A61K 39/116; A61K 39/39; A61K 47/4833; A61K 39/02
See application file for complete search history.

(56) References Cited

U.S. PATENT DOCUMENTS

| | | |
|---|---|---|
| 4,673,574 A | 6/1987 | Anderson |
| 4,902,506 A | 2/1990 | Anderson et al. |
| 4,912,094 A | 3/1990 | Myers et al. |
| 5,057,540 A | 10/1991 | Kensil et al. |
| 5,153,312 A | 10/1992 | Porro |
| 5,614,382 A | 3/1997 | Metcalf |
| 5,769,047 A | 6/1998 | Zoche |
| 5,847,112 A | 8/1998 | Kniskern et al. |
| 6,113,918 A | 9/2000 | Johnson et al. |
| 6,207,646 B1 | 3/2001 | Krieg et al. |
| 8,808,708 B2 * | 8/2014 | Hausdorff ............ A61K 39/092 424/184.1 |
| 9,480,736 B2 | 11/2016 | Hausdorff et al. |
| 9,492,558 B2 | 11/2016 | Costantino |
| 2003/0147922 A1 | 8/2003 | Capiau et al. |
| 2004/0202668 A1 | 10/2004 | Boutriau et al. |
| 2006/0028380 A1 | 2/2006 | Harano |
| 2006/0228380 A1 | 10/2006 | Hausdorff et al. |
| 2007/0184072 A1 | 8/2007 | Hausdorff et al. |
| 2007/0231340 A1 | 10/2007 | Hausdorff et al. |
| 2008/0069835 A1 | 3/2008 | Boutriau et al. |
| 2009/0010959 A1 | 1/2009 | Biemans et al. |
| 2009/0017072 A1 | 1/2009 | Biemans et al. |
| 2009/0130137 A1 | 5/2009 | Hausdorff et al. |
| 2010/0209450 A1 | 8/2010 | Biemans et al. |
| 2010/0316666 A1 | 12/2010 | Hausdorff et al. |
| 2011/0195086 A1 | 8/2011 | Caulfield et al. |
| 2011/0243976 A1 | 10/2011 | Donati et al. |
| 2012/0052088 A1 | 3/2012 | Davis et al. |

(Continued)

FOREIGN PATENT DOCUMENTS

| | | |
|---|---|---|
| CN | 101180079 A | 5/2008 |
| CN | 101590224 A | 12/2009 |

(Continued)

OTHER PUBLICATIONS

Mantese et al J Pediatr . 2009; 85(6):495-502.*
Saha et al Clin Infect Dis 2009:48 (Suppl 2) S75.*
Harboe, Zitta B. et al. "Temporal Trends in Invasive Pneumococcal Disease and Pneumococcal Serotypes over 7 Decades" Clinical Infectious Diseases 2010;50;329-27, pp. 329-337, (8 pages).
Saha, Samir K. et al. "*Streptococcus pneumoniae* Serotype-2 Childhood Meningitis in Bangladesh: A Newly Recognized Pneumococcal Infection Threat" PLos One, Mar. 2012; vol. 7; Issue 3; pp. 1-7 (8 pages).
International Search Report (PCT/ISA/210) mailed on Sep. 30, 2013, by the Republic of Korea Patent Office as the International Searching Authority for International Application No. PCT/KR2013/005392.
Written Opinion (PCT/ISA/237) mailed on Sep. 30, 2013, by the Republic of Korea 2'1Patent Office as the International Searching Authority for International Application No. PCT/KR2013/005392.

(Continued)

*Primary Examiner* — Padmavathi Baskar
(74) *Attorney, Agent, or Firm* — Buchanan Ingersoll & Rooney PC

(57) ABSTRACT

Provided is an immunogenic composition comprising 15 different polysaccharide-protein conjugates. Each of the conjugates comprises a capsular polysaccharide prepared from different serotype *Streptococcus pneumoniae* conjugated to a carrier protein, that is, serotypes 1, 2, 3, 4, 5, 6A, 6B, 7F, 9N, 9V, 14, 18C, 19A, 19F and 23F. An immunogenic composition formulated into a vaccine comprising an aluminum-based adjuvant increases application range with respect to pneumococcal diseases in infants and children.

12 Claims, 8 Drawing Sheets

(56) References Cited

U.S. PATENT DOCUMENTS

| | | |
|---|---|---|
| 2012/0189654 A1 | 7/2012 | Biemans et al. |
| 2012/0237542 A1 | 9/2012 | Hausdorff et al. |
| 2012/0301502 A1 | 11/2012 | Caulfield et al. |
| 2013/0072881 A1 | 3/2013 | Khandke et al. |

FOREIGN PATENT DOCUMENTS

| | | |
|---|---|---|
| EP | 2687228 A2 | 1/2014 |
| JP | 2007/535531 A | 12/2007 |
| JP | 2008-535838 | 9/2008 |
| JP | 2009/532439 A | 9/2009 |
| JP | 2010/531329 A | 9/2010 |
| JP | 2010260849 A | 11/2010 |
| KR | 10/0642044 B1 | 11/2006 |
| KR | 10/0870280 B1 | 11/2008 |
| WO | WO 90/14837 A1 | 12/1990 |
| WO | WO 92/19265 A1 | 11/1992 |
| WO | WO 93/13302 A1 | 7/1993 |
| WO | WO 00/18434 A1 | 4/2000 |
| WO | 00/56359 A2 | 9/2000 |
| WO | 01/68128 A1 | 9/2001 |
| WO | WO 02/053761 A2 | 7/2002 |
| WO | 02/080965 A2 | 10/2002 |
| WO | WO 02/083855 A2 | 10/2002 |
| WO | WO 02/098368 A2 | 12/2002 |
| WO | WO 02/098369 A2 | 12/2002 |
| WO | WO 2004/083251 A2 | 9/2004 |
| WO | 2006082530 A2 | 8/2006 |
| WO | 2006/110381 A1 | 10/2006 |
| WO | WO2007/000342 * | 1/2007 |
| WO | 2007/071707 A2 | 6/2007 |
| WO | 2007/116028 A2 | 10/2007 |
| WO | 2009/000825 A2 | 12/2008 |
| WO | 2009000826 A1 | 12/2008 |
| WO | 2010-125480 A1 | 11/2010 |
| WO | 2011/100151 A1 | 8/2011 |
| WO | WO 2011/15176 | 12/2011 |
| WO | 2012-078482 A1 | 6/2012 |

OTHER PUBLICATIONS

Japanese Office Action dated Dec. 1, 2015, issued in corresponding Japanese Application No. 2015-518332.

Extended European Search Report dated Dec. 22, 2015, issued in corresponding European Application No. 13806263.3.

Office Action dated Oct. 7, 2015 received in corresponding Canadian Patent Application No. 2,877,648.

Selva et al., "Serotype 3 is a common serotype causing invasive pneumococcal disease in children less than 5 years old, as identified by real-time PCR", Eur. J. Clin. Microbial Infect. Dis., 2012, 31(7), 1487-1495. (epublished Nov. 4, 2011).

Duggan, "Pneumococcal polysaccharide conjugate vaccine (13-valent, absorbed) [Prevenar 13®]", Drugs, 2010, 70 (15), 1973-1986.

Weinberger et al., "Association of serotype with risk of death due to pneumococcal pneumonia: A meta-analysis", Clin. Infect. Dis., 2010, 51(6), 692-699.

Koskela et al., "Comparison of ELISA and RIA for measurement of pneumococcal antibodies before and after vaccination with 14-valent pneumococcal capsular polysaccharide vaccine", J. Clin. Pathol., 1981, 34, 93-98.

Russian Office Action issued by the Patent Office of the Russian Federation dated Mar. 18, 2016 in corresponding Russian Patent Application No. 201500140/15, with English translation (13 pages).

Skinner et al., "Pre-clinical evaluation of a 15-valent pneumococcal conjugate vaccine (PCV15-CRM197) in an infant-rhesus monkey immunogenicity model", Vaccine, 2011, 29, pp. 8870-8876.

Office Action dated Nov. 1, 2016, by the Japanese Patent Office in corresponding Japanese Patent Application No. 2015-547845. (3 pages).

A. Pawlowski et al., "Preparation of pneumococcal capsular polysaccharide-protein conjugate vaccines utilizing new fragmentation and conjugate technologies", Vaccine, Mar. 17, 2000, pp. 1873-1885, vol. 18, No. 18.

Office Action (Inquiry) dated Oct. 12, 2016, by the Russian Patent Office in corresponding Russian Patent Application No. 2015121771/15, and an English Translation of the Office Action. (11 pages).

Hicks, Lauri A. et al. "Incidence of Pneumococcal Disease Due to Non-Pneumococcal Conjugate Vaccine (PCV7) Serotypes in the United States during the Era of Widespread PCV7 Vaccination, 1998-2004," The Journal of Infectious Diseases; 2007; 196; pp. 1346-1354 (8 pages).

Jacobs, Michael R. et al. "Emergence of *Streptococcus pneumoniae* Serotypes 19A, 6C and 22F and Serogroup 15 in Cleveland, Ohio, in Relation to Introduction of the Protein-Conjugated Pneumococcal Vaccine," Clinical Infectious Diseases 2008; 47; pp. 1388-1395 (7 pages).

Extended European search report dated Jun. 2, 2016 of the European patent application No. 13862871.4.

Office Action dated Jun. 6, 2016 of the corresponding Canadian patent application No. 2,894,532.

Office Action dated Mar. 15, 2016 in corresponding Japanese Application No. 2015-547845.

Albert Jan van Hoek et al., "Effect of Serotype on Focus and Mortality of Invasive Pneumococcal Disease: Coverage of Different Vaccines and Insight into Non-Vaccine Serotypes", PLoS One, Jul. 16, 2012, vol. 7, No. 7, e39150, pp. 1-10.

International Search Report (PCT/ISA/210) dated Mar. 17, 2014, by the Korean Patent Office as the International Searching Authority for International Application No. PCT/KR2013/011195.

Written Opinion (PCT/ISA/237) dated Mar. 17, 2014, by the Korean Patent Office as the International Searching Authority for International Application No. PCT/KR2013/011195.

Baylor, et al., 2002, Aluminum salts in vaccines—US perspective, Vaccine 20: S18-S23.

Pollabauer et al., 2009, The influence of carrier protein on the immunogenicity of simultaneously administered conjugate vaccines; Vaccine 27: 1674-1679.

Office Action (Decision of Refusal) dated Sep. 6, 2016, by the Japanes Patent Office in corresponding Japanese Patent Application No. 2015-547844, and an English Translation of the Office Action. (5 pages).

Office Action (Notification of the First Office Action) dated Sep. 27, 2016, by the State Intellectual Property Office of the People's Republic of China in corresponding Chinese Patent Application No. 201380064974.X, and an English Translation of the Office Action. (15 pages).

Office Action dated Jun. 6, 2016, by the Canadian Patent Office in corresponding Canadia Patent Application No. 2,896,528. (7 pages).

Office Action dated May 31, 2016 by the Russian Patent Office in corresponding Russian Patent Application No. 2015121772, and an English Translation of the Office Action. (13 pages).

Office Action dated Apr. 19, 2016, by the Japanese Patent Office in Japanese Patent Application No. 2015-547844. (2 pages).

Extended European Search Report dated May 3, 2015, issued by the European Patent Office in corresponding European Application No. EP 13862717.9-1460/2932979. (14 pages).

Oosterhuis-Kafeja et al., Immunogenicity, efficacy, safety and effectiveness of pneumococcal conjugate vaccines (1998-2006), Vaccine, 25, (2007), pp. 2194-2212.

International Search Report (PCT/ISA/210) dated Feb. 28, 2014, by the Korean Patent Office as the International Searching Authority for International Application No. PCT/KR2013/011194.

Written Opinion (PCT/ISA/237) dated Feb. 28, 2014, by the Korean Patent Office as the International Searching Authority for International Application No. PCT/KR2013/011194.

Final Office Action dated Apr. 26, 2017, issued in U.S. Appl. No. 14/651,021.

Non-Final Office Action dated Nov. 10, 2016, issued in U.S. Appl. No. 14/651,021.

Non-Final Office Action dated Apr. 17, 2017, issued in U.S. Appl. No. 14/651,046.

Advisory Action dated Aug. 18, 2016, issued in U.S. Appl. No. 14,651,046.

Final Office Action dated May 10, 2016, issued in U.S. Appl. No. 14/651,046.

(56) References Cited

OTHER PUBLICATIONS

Non-Final Office Action dated Dec. 23, 2015, issued in U.S. Appl. No. 14/651,046.
Opposition dated Aug. 23, 2017 of the European Patent Application No. 13806263.3.
Final Office Action dated Aug. 17, 2017 of the U.S. Appl. No. 14/651,021.
Final Office Action dated Aug. 30, 2017 of the U.S. Appl. No. 14/651,046.
Park, Chulmin et al., "Comparative evaluation of a newly developed 13-valent pneumococcal conjugate vaccine in a mouse model" Human Vaccines & Immunotherapeutics, vol. 13, No. 5, Dec. 14, 2016.
Bagnoli, Fabio et al., "A Second Plus Type in *Streptococcus pneumoniae* is Prevalent in Emerging Serotypes and Mediates Adhesion to Hast Cells" Journal of Bacteriology, vol. 190, No. 15, May 30, 2008.
Bryant, Kristina et al., "Safety and immunogenicity of a 13-Valent Pneumococcal Conjugate Vaccine" Pediatrics, vol. 125, No. 5, May 2010.
Sucher, Allana et al., "Prevnar 13, the New 13-Valent Pneumococcal Conjugate Vaccine" Annal of Pharmacotherapy, vol. 45, No. 12, Nov. 1, 2012.
Wyeth Pharmaceuticals Inc., "Highlights of Prescribing Information" Jan. 4, 2010, [cited Dec. 21, 2010]. http://www.miamimed.com/cmsAdmin/uploads/274112-01_(PrevnaM3_Package_Insert_PDF).pdf.
Wilson, Duff, "Vaccine Approved for Child Infections" Feb. 24, 2010, [cited Aug. 14, 2017]. http://www.nytimes.com/2010/02/25/business/25vaccine.html.
PharmiWeb, "Pfizer Receives PDA Approval for Prevnar 13™ for the Prevention of Invasive Pneumococcal Disease in Infants and Young Children" Feb. 24, 2010, [cited Aug. 2, 2017]. http://www.pharmiweb.com/PressReleases/pressrel.asp?ROW_ID=17021#.WYHKOfLrtgU.
Office Action dated Jul. 17, 2017 of Columbia Patent Application No. 15-154489.
Nuorti et al., Prevention of Pneumococcal Disease Among Infants and Children—Use of 13-Valent Pneumococcal Conjugate Vaccine and 23-Valent Pneumococcal Polysaccharide Vaccine: Recommendations of the Advisory Committee on Immunization Practices (ACIP), Morbidity and Morality Weekly Report (MMWR), Dec. 10, 2010, pp. 1-28, vol. 59(RR11), No. 1-18, Centers for Disease Control and Prevention.
Office Action dated Sep. 20, 2017, by the Canadian Intellectual Property Office in Canadian Patent Application No. 2,894,532. (4 pages).
Office Action dated Sep. 15, 2017, by the Canadian Intellectual Property Office in Canadian Patent Application No. 2,896,528. (4 pages).

\* cited by examiner

POLYVALENT PNEUMOCOCCAL POLYSACCHARIDE-PROTEIN CONJUGATE COMPOSITION

TECHNICAL FIELD

The present invention relates to a multivalent immunogenic composition comprising: 15 distinct polysaccharide-protein conjugates prepared by conjugating capsular polysaccharide derived from *Streptococcus pneumoniae* serotypes, 1, 2, 3, 4, 5, 6A, 6B, 7F, 9N, 9V, 14, 18C, 19A, 19F and 23F to a carrier protein such as $CRM_{197}$. The present invention relates generally to the field of medicine, and specifically to microbiology, immunology, vaccines and the prevention of pneumococcal disease in infants, children, and adults by immunization.

BACKGROUND ART

*Streptococcus pneumoniae* is a leading cause of pneumonia. According to 2010 Mortality Trend by Cause published by The National Statistical Office, pneumonia was one of the top 10 causes of death, with 14.9 deaths per 100,000 people, which is an 82.9% increase from 2000. The World Health Organization (WHO) also estimated in 2012 that globally, 476,000 HIV negative children younger than 5 years of age died from infection by *Streptococcus pneumoniae*, which accounts for 5% of all-cause child mortality for children under five.

In 1977, Dr. Robert Austrian developed a 14-valent pneumococcal polysaccharide vaccine in order to prevent pneumococcal disease and then the vaccine evolved to a 23-valent polysaccharide vaccine. The multivalent pneumococcal polysaccharide vaccines have proved valuable in preventing pneumococcal disease in elderly adults and high-risk patients. However, infants and young children respond poorly to most pneumococcal polysaccharides due to T-cell independent immune response. The 7-valent pneumococcal conjugate vaccine (7vPnC, Prevnar®) contains the capsular polysaccharides from the seven most prevalent serotypes 4, 6B, 9V, 14, 18C, 19F and 23F. Since approved in the U.S. in 2000, Prevnar has been demonstrated to be highly immunogenic and effective against invasive disease and otitis media in infants and young children. This vaccine is now approved in about 80 countries around the world. Prevnar covers approximately 80-90%, 60-80%, and 40-80% of invasive pneumococcal disease (IPD) in the US, Europe, and other regions of the world, respectively. As expected, surveillance data gathered in the years following Prevnar's introduction has clearly demonstrated a reduction of invasive pneumococcal disease caused by the serotypes covered by Prevnar in the US. However, the coverage of the serotypes was limited in some regions and invasive pneumococcal diseases caused by the serotypes that are not covered by Prevnar, in particular 19A, have increased.

The Advisory Committee on Immunization Practices (ACIP) announced in February, 2010 its recommendation of a newly approved 13-valent pneumococcal conjugate vaccine (PCV-13) for vaccination. PCV-13 is a pneumococcal conjugate vaccine comprising six additional serotypes (1, 3, 5, 6A, 7F, 19A) in addition to the seven serotypes (4, 6B, 9V, 14, 18C, 19F, 23F) comprised in Prevnar. According to US Active Bacterial Core surveillance (ABCs), a total of 64% in the IPD cases known as the pathogenic serotypes among children of younger than 5 years of age is covered by PCV-13. In 2007, only 70 cases among 4600 IPDs in children younger than 5 years of age were covered by PCV7, while 2900 cases were covered by PCV-13, which accounts for the majority. Now, a 15-valent pneumococcal conjugate vaccine is under development which covers additional serotypes whose incidence increases with serotype replacement.

DETAILED DESCRIPTION OF THE INVENTION

Accordingly, the present invention provides a multivalent immunogenic composition for the prevention of pneumococcal disease in infants, children and adults, comprising capsule polysaccharides derived from 15 pneumococcal serotypes including serotypes 2 and 9N. Specifically, the present invention provides a 15-valent pneumococcal conjugate (PCV-15) composition comprising serotypes 1, 2, 3, 4, 5, 6A, 6B, 7F, 9N, 9V, 14, 18C, 19A, 19F and 23F.

Technical Solution

According to one aspect of the invention, provided is a multivalent immunogenic composition, comprising 15 distinctive polysaccharide-protein conjugates together with a physiologically acceptable vehicle, wherein each of the conjugates comprises a capsular polysaccharide derived from a different serotype of *Streptococcus pneumoniae* conjugated to a carrier protein, and the capsular polysaccharides are prepared from serotypes 1, 2, 3, 4, 5, 6A, 6B, 7F, 9N, 9V, 14, 18C, 19A, 19F and 23F.

In the multivalent immunogenic composition according to the present invention, the carrier protein may be $CRM_{197}$. The multivalent immunogenic composition according to the present invention may further comprise an adjuvant, for example, the adjuvant comprising an aluminum-based adjuvant. The adjuvant may be selected from the group consisting of aluminum phosphate, aluminum sulfate and aluminum hydroxide, and preferably, aluminum phosphate.

According to a further aspect of the invention, provided is a pharmaceutical composition for inducing an immune response to a *Streptococcus pneumoniae* capsular polysaccharide conjugate, comprising an immunologically effective amount of said immunogenic composition.

In one embodiment, the pharmaceutical composition may be an immunogenic composition formulated to contain: 2 μg of each saccharide, except for 6B at 4 μg; approximately 34 μg $CRM_{197}$ carrier protein; 0.125 mg of elemental aluminum (0.5 mg aluminum phosphate) adjuvant; and sodium chloride and sodium succinate buffer as excipients.

Technical Effect

The multivalent-immunogenic composition comprises capsular polysaccharides derived from 15 distinctive pneumococcal serotypes including serotypes 2 and 9N, thereby leading to elevated serum IgG titer and functional antibody activity. Therefore, the multivalent immunogenic composition can be advantageously used for prevention of pneumococcal disease in infants, children and adults.

MODE FOR INVENTION

Figure 1:
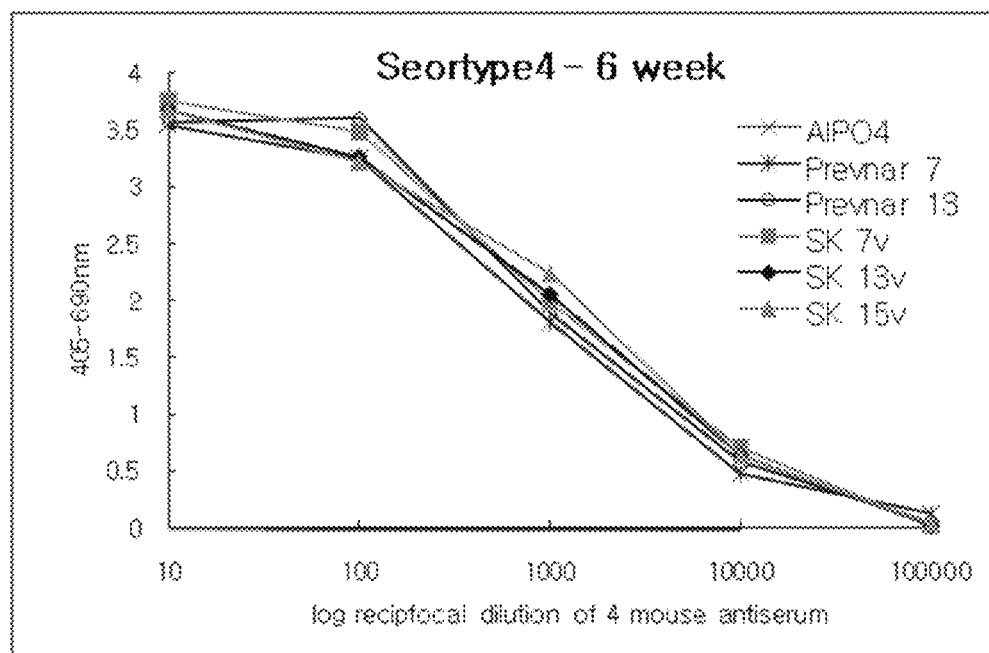
FIGS. 1 to 15 show the level of serotype-specific IgG measured 3 weeks after secondary injection (i.e., a total of 6 weeks) of the vaccine composition of the present invention and the comparative example (Prevnar 7 and Prevnar 13).

Serotype replacement has been made by some serotypes with antibiotic resistance and multiple drug resistance.

Regional difference in serotype distribution has led to difference in coverage of Prevnar by region. (Harboe Z B, Benfield T L, Valentiner-Branth P, et al. Temporal Trends in Invasive Pneumococcal Disease and Pneumococcal Serotypes over 7 Decades. Clin Infect Dis 2010; 50:329-37). Thus, there is no reason to remove any of the serotypes in the existing pneumococcal conjugate vaccines. Rather, there is a need to further expand the coverage by addition of serotypes.

In 2008, the Pneumococcal Global Serotype Project (GSP) announced a report based on the IPD data selected from 1980 to 2007, showing that, following serotype 18C, serotype 2 was the $11^{th}$ highest incidence serotype among the top 20 global serotypes. In addition, Samir K. Saha et al. reported that serotype 2 may become a threat because the serotype 2 has a high probability of causing pneumococcal meningitis in Bangladesh but is not included in any pneumococcal conjugate vaccine (Saha S K, Al Emran H M, Hossain B, Darmstadt G L, Saha S, et al. (2012) *Streptococcus pneumoniae* Serotype-2 Childhood Meningitis in Bangladesh: A Newly Recognized Pneumococcal Infection Threat. PLoS ONE 2012; 7(3): e32134). Thus, if serotype 2 is included, the number of pneumococcal diseases can be reduced and further be prepared for the serotype replacement that may occur with the vaccination by PCV-13.

Pneumococcal serotypes show different distribution patterns by age. In particular, serotype 9N has been found to be relatively important in infants aged 0 to 23 months, compared to children aged 24 to 59 months. Serotype 9N was the $14^{th}$ most common following the 13 serotypes included in PCV-13. This indicates that inclusion of serotype 9N will contribute to reduction in pneumococcal diseases, in particular among infants.

The present invention provides a multivalent immunogenic composition comprising capsular polysaccharides derived from 15 pneumococcal serotypes including serotypes 2 and 9N. Specifically, the present invention provides a multivalent immunogenic composition, comprising: 15 distinct polysaccharide-protein conjugates, together with a physiologically acceptable vehicle, wherein each of the conjugates comprises a capsular polysaccharide from a different serotype of *Streptococcus pneumoniae* conjugated to a carrier protein, and the capsular polysaccharides are prepared from serotypes 1, 2, 3, 4, 5, 6A, 6B, 7F, 9N, 9V, 14, 18C, 19A, 19F and 23F.

Capsular polysaccharides may be prepared by standard techniques known to those skilled in the art. Capsular polysaccharides can be reduced in size in order to decrease the viscosity or increase the solubility of activated capsular polysaccharides. In the present invention, capsular polysaccharides are prepared from serotypes 1, 2, 3, 4, 5, 6A, 6B, 7F, 9N, 9V, 14, 18C, 19A, 19F and 23F of *Streptococcus pneumoniae*. These pneumococcal conjugates are prepared by separate processes and formulated into a single dosage formulation. For example, each pneumococcal polysaccharide serotype is grown in a soy-based medium and then is purified through centrifugation, precipitation, and ultra-filtration.

Carrier proteins are preferably proteins that are non-toxic and non-reactogenic and obtainable in sufficient amount and purity. Carrier proteins should be amenable to standard conjugation procedures. In the multivalent immunogenic composition of the present invention, the carrier protein may be $CRM_{197}$. $CRM_{197}$ is a non-toxic variant (i.e., toxoid) of diphtheria toxin isolated from cultures of *Corynebacterium diphteria* strain C7 (β197) grown on casamino acids and yeast extract-based medium. CRM197 is purified through ultra-filtration, ammonium sulfate precipitation, and ion-exchange chromatography. Alternatively, CRM197 is prepared recombinantly in accordance with U.S. Pat. No. 5,614,382.

Other diphtheria toxoids are also suitable for use as carrier proteins. Other suitable carrier proteins include inactivated bacterial toxins such as tetanus toxoid, pertussis toxoid; cholera toxoid (WO2004/083251). *E. coli* LT, *E. coli* ST, and exotoxin A from *Pseudomonas aeruginosa*. Bacterial outer membrane proteins such as outer membrane complex c (OMPC), porins, transferrin binding proteins, pneumolysin, pneumococcal surface protein A (PspA), pneumococcal adhesin protein (PsaA), C5a peptidase from Group A or Group B *streptococcus*, or *Haemophilus influenzae* protein D, can also be used. Other proteins, such as ovalbumin, keyhole limpet hemocyanin (KLH), bovine serum albumin (BSA) or purified protein derivative of tuberculin (PPD) can also be used as carrier proteins. Diphtheria toxin variants such as $CRM_{173}$, $CRM_{228}$) and $CRM_{45}$ can be used as a carrier protein.

In order to prepare polysaccharides for reaction with a carrier protein, purified polysaccharides are chemically activated. Once activated, each capsular polysaccharide is separately conjugated to a carrier protein to form a glycoconjugate. In one embodiment, each capsular polysaccharide is conjugated to the same carrier protein. The chemical activation of the polysaccharides and subsequent conjugation to the carrier protein are achieved by conventional means (for example, U.S. Pat. Nos. 4,673,574 and 4,902,506). Hydroxyl groups in the polysaccharides are oxidized to aldehyde groups by oxidizing agents such as periodates (including sodium periodate, potassium periodate, calcium periodate or periodic acid). The chemical activation leads to irregular oxidative degradation of adjacent hydroxyl groups. The conjugation is achieved by reductive amination. For example, the activated capsular polysaccharides and the carrier protein are reacted with a reducing agent such as sodium cyanoborohydride. Unreacted aldehyde groups can be removed by addition of a strong oxidizing agent.

After conjugation of the capsular polysaccharide to the carrier protein, the polysaccharide-protein conjugates are purified (enriched with respect to the amount of polysaccharide-protein conjugate) by a variety of techniques. These techniques include concentration/diafiltration, column chromatography, and depth filtration. The purified polysaccharide-protein conjugates are compounded to formulate the immunogenic composition of the present invention, which can be used as a vaccine. Formulation of the immunogenic composition of the present invention can be accomplished using art-recognized methods. For instance, the 15 individual pneumococcal conjugates can be formulated with a physiologically acceptable vehicle to prepare the composition. Examples of such vehicles include, but are not limited to, water, buffered saline, polyols (e.g., glycerol, propylene glycol, liquid polyethylene glycol) and dextrose solutions.

In one embodiment, the immunogenic composition of the present invention may comprise one or more adjuvants. As defined herein, an "adjuvant" is a substance that serves to enhance the immunogenicity of an immunogenic composition of this invention. Thus, adjuvants are often given to boost the immune response and are well known to the skilled artisan. Suitable adjuvants to enhance effectiveness of the composition include, but are not limited to:

(1) aluminum salts (alum), such as aluminum hydroxide, aluminum phosphate, aluminum sulfate, etc.;

(2) oil-in-water emulsion formulations (with or without other specific immunostimulating agents such as muramyl peptides (defined below) or bacterial cell wall components), such as, for example, (a) MF59 (WO 90/14837), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalene, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Corixa, Hamilton, Mont.) containing 2% Squalene, 0.2% Tween 80, and one or more bacterial cell wall components from the group consisting of 3-O-deacylated monophosphorylipid A (MPL™) described in U.S. Pat. No. 4,912,094 (Corixa), trehalose dimycolate (TDM), and cell wall skeleton (CWS), preferably MPL+CWS (Detox™);

(3) saponin adjuvants, such as Quil A or STIMULON™ QS-21 (Antigenics, Framingham, Mass.) (U.S. Pat. No. 5,057,540) or particles generated therefrom such as ISCOMs (immunostimulating complexes);

(4) bacterial lipopolysaccharides, synthetic lipid A analogs such as aminoalkyl glucosamine phosphate compounds (AGP), or derivatives or analogs thereof, which are available from Corixa, and which are described in U.S. Pat. No. 6,113,918; one such AGP is 2-[(R)-3-Tetradecanoyloxytetradecanoylamino]ethyl 2-Deoxy-4-0-phosphono-3-0-[(R)-3-tetradecanoyloxytetradecanoy]-2-[(R)-3-tetr adecanoyloxytetradecanoylamino]-b-D-glucopyranoside, which is also known as 529 (formerly known as RC529), which is formulated as an aqueous form or as a stable emulsion, (5) synthetic polynucleotides such as oligonucleotides containing CpG motif(s) (U.S. Pat. No. 6,207,646);

(6) cytokines, such as interleukins (e.g., IL-1, IL-2, IL-4, IL-5, IL-6, IL-7, IL-12, IL-15, IL-18, etc.), interferons (e.g., gamma interferon), granulocyte macrophage colony stimulating factor (GM-CSF), macrophage colony stimulating factor (M-CSF), tumor necrosis factor (TNF), costimulatory molecules B7-1 and B7-2, etc.;

(7) detoxified mutants of a bacterial ADP-ribosylating toxin such as a cholera toxin (CT) either in a wild-type or mutant form, for example, where the glutamic acid at amino acid position 29 is replaced by another amino acid, preferably a histidine, in accordance with WO 00/18434 (see also WO 02/098368 and WO 02/098369), a pertussis toxin (PT), or an *E. coli* heat-labile toxin (LT), particularly LT-K63, LT-R72, CT-S109, PT-K9/G129 (see, e.g., WO 93/13302 and WO 92/19265); and (8) complement components such as trimer of complement component C3d.

Muramyl peptides include, but are not limited to, N-acetyl-muramyl-L-threonyl-D-isoglutamine (thr-MDP), N-acetyl-normuramyl-L-alanine-2-(1'-2'dipalmitoyl-sn-glycero-3-hydroxyphosphoryloxy)-ethylamine (MTP-PE), etc.

In a specific embodiment, an aluminum salt is used as an adjuvant. Aluminum salt adjuvant may be an alum-precipitated vaccine or alum-adsorbed vaccine. Aluminum salts include, but are not limited to, hydrated alumina, alumina trihydrate (ATH), aluminum hydrate, aluminum trihydrate, Alhydrogel, Superfos, Amphojel, aluminum hydroxide (III), aluminum hydroxyphosphate sulfate(Aluminum Phosphate Adjuvant (APA)), and amorphous alumina. APA is a suspension of aluminum hydroxyphosphate. If aluminum chloride and sodium phosphate are mixed in a ratio of 1:1, aluminum hydroxyphosphate sulfate is precipitated. The precipitates are sized to 2-8 µm by using high shear mixer and dialyzed with physiological saline, followed by sterilization. In one embodiment, commercially available Al(OH)$_3$ (for example, Alhydrogel or Superfos) is used to adsorb proteins. 50-200 g of protein can be adsorbed per 1 mg of aluminum hydroxide, and this ratio is dependent on isoelectric point (pI) of proteins and pH of solvents. Proteins of low pI are strongly adsorbed compared to proteins of high pI. Aluminum salts form an antigen depot that slowly releases antigens over 2 to 3 weeks, nonspecifically activating phagocytes, complements and the congenital immune mechanism.

The present invention provides a pharmaceutical composition (for example, a vaccine formulation) for inducing an immune response to a *Streptococcus pneumoniae* capsular polysaccharide conjugate, comprising an immunologically effective amount of the immunogenic composition.

The vaccine formulations of the present invention can be used to protect or treat a human susceptible to pneumococcal infection, by administering the vaccine via a systemic or mucosal route. As defined herein, the term "effective dose" refers to the amount required to induce antibody to a level sufficient to significantly reduce the probability of *Streptococcus pneumonia* infection or severity thereof. These administrations can include injection via the intramuscular, intraperitoneal, intradermal or subcutaneous routes; or via mucosal administration to the oral/alimentary, respiratory or genitourinary tracts.

In one embodiment, intranasal administration is used for the treatment of pneumonia or otitis media since nasopharyngeal carriage of pneumococci can be more effectively prevented, thus attenuating infection at its earliest stage. The amount of conjugate in each vaccine dose is selected as an amount that induces an immunoprotective response without significant, adverse effects. Such an amount can vary depending upon the pneumococcal serotype. Generally, each dose will comprise 0.1 to 100 µg of polysaccharide, particularly 0.1 to 10 µg, and more particularly 1 to 5 µg. Optimal amounts of components for a particular vaccine can be ascertained by standard studies involving observation of appropriate immune responses in subjects. For example, the amount for vaccination of a human subject can be determined by extrapolating the animal test result. In addition, the dosage can be determined empirically.

In a particular embodiment of the present invention, the vaccine composition is a sterile liquid formulation of pneumococcal capsular polysaccharides of serotypes 1, 3, 4, 5, 6A, 6B, 7F, 9V, 14, 18C, 19A, 19F, and 23F individually conjugated to CRM197. Each 0.5 mL dose is formulated to contain: 2 µg of each saccharide, except for 6B at 4 µg; approximately 34 µg CRM197 carrier protein; 0.125 mg of elemental aluminum (0.5 mg aluminum phosphate) adjuvant; and sodium chloride and sodium succinate buffer as excipients. The liquid is filled into single dose syringes without a preservative. After shaking, the vaccine is a homogeneous, white suspension ready for intramuscular administration.

In a further embodiment, the composition of the present invention can be administered in a single injection. For example, the vaccine composition of the present invention can be administered 2, 3, 4, or more times at appropriately spaced intervals, such as, with a 1, 2, 3, 4, 5, or 6 month interval or combination thereof. The immunization schedule can follow that designated for the Prevnar vaccine. For example, the routine schedule for infants and toddlers against invasive disease caused by *S. pneumoniae* due to the serotypes included in the Prevnar vaccine is at 2, 4, 6 and 12-15 months of age. Thus, in this aspect, the composition is administered 4 times, i.e., at 2, 4, 6, and 12-15 months of age.

The compositions of the present invention may also include one or more proteins from *Streptococcus pneumoniae*. Examples of *Streptococcus pneumoniae* proteins suitable for inclusion include those identified in International Patent Application WO02/083855, as well as that described in International Patent Application WO02/053761.

The composition of the present invention can be administered to a subject via one or more administration routes known to one of ordinary skill in the art such as a parenteral, transdermal, or transmucosal, intranasal, intramuscular, intraperitoneal, intracutaneous, intravenous, or subcutaneous route and be formulated accordingly. In one embodiment, the composition of the present invention can be administered as a liquid formulation by intramuscular, intraperitoneal, subcutaneous, intravenous, intraarterial, or transdermal injection or respiratory mucosal injection. The liquid formulation for injection includes a solution or the like.

The composition of the present invention can be formulated in a form of a unit dose vial, multiple dose vial, or pre-filled syringe. A pharmaceutically acceptable carrier for a liquid formulation includes aqueous or nonaqueous solvent, suspension, emulsion or oil. Examples of a nonaqueous solvent include propylene glycol, polyethylene glycol, and ethyl oleate. Aqueous carriers include water, alcohol/aqueous solvent, emulsion, or suspension, physiological saline, buffer solution. Examples of oil include vegetable or animal oil, peanut oil, soybean oil, olive oil, sunflower oil, liver oil, synthetic oil such as marine oil, and lipids obtained from milk or eggs. The pharmaceutical composition may be isotonic, hypertonic or hypotonic. However, it is desirable that the pharmaceutical composition for infusion or injection is basically isotonic. Thus, isotonicity or hypertonicity may be advantageous for storage of the composition. When the pharmaceutical composition is hypertonic, the composition can be diluted to isotonicity before administration. Tonicity agent may be ionic tonicity agent such as salt or non-ionic tonicity agent such as carbohydrate. The ionic tonicity agent includes sodium chloride, calcium chloride, potassium chloride, and magnesium chloride, but is not limited thereto. Nonionic tonicity agent includes sorbitol and glycerol, but is not limited thereto. Preferably, at least one pharmaceutically acceptable buffer is included. For example, when the pharmaceutical composition is an infusion or injection, it is preferable to be formulated in a buffer with buffering capacity at pH 4 to 10, such as pH 5-9 or 6-8. The buffer can be selected from the group consisting of TRIS, acetate, glutamate, lactate, maleate, tartrate, phosphate, citrate, carbonate, glycinate, histidine, glycine, succinate, and triethanolamine buffer solution.

In particular, if the pharmaceutical composition is for parenteral administration, a buffer may be selected from those suitable for United States Pharmacopeia (USP). For example, the buffer may be selected from the group consisting of monobasic acid such as acetic acid, benzoic acid, gluconic acid, glyceric acid, and lactic acid; polybasic acid such as aconitic acid, adipic acid, ascorbic acid, carbonic acid, glutamic acid, malic acid, succinic acid, and tartaric acid; and base such as ammonia, diethanolamine, glycine, triethanolamine, and TRIS. For parenteral administration, vehicles (for subcutaneous, intravenous, intraarticular, and intramuscular injection) include sodium chloride solution, Ringer's dextrose solution, dextrose and sodium chloride, lactated Ringer's solution and fixed oils. Vehicles for intravenous administration include Ringer's dextrose solution or a similar dextrose based infusion solution, nutritional supplements and electrolyte supplements. The example includes a sterile liquid such as water and oil, with or without a surface active agent and pharmaceutically acceptable adjuvant. Generally, water, physiological saline, dextrose solution, related sugar solution, and glycols such as propylene glycol or polyethylene glycol, in particular, polysorbate 80 are suitable for an injection. Examples of oil include animal and vegetable oil, peanut oil, soybean oil, olive oil, sunflower oil, liver oil, synthetic oil such as marine oil and lipids from milk or eggs.

The formulation of the present invention may comprise surface active agents. Preferably, polyoxyethylene sorbitan ester (generally referred to as Tweens), in particular, polysorbate 20 and polysorbate 80; copolymers (such as DOWFAX™) of ethylene oxide (EO), propylene oxide (PO), butylenes oxide (BO); oxtocynols with different repeats of ethoxy(oxy-1,2-ethanediyl) group, in particular, octoxynol-9(Triton-100); ethylphenoxypolyethoxyethanol (IGEPAL CA-630/NP-40); phospholipid such as lecithin; nonylphenol ethoxylate such as Tergitol™ NP series; lauryl, cetyl, stearyl, oleyl alcohol-derived polyoxyethylene fatty ether (Brij surfactant), in particular, triethyleneglycol monolauryl ether (Brij 30); sorbitan ether known as SPAN, in particular, sorbitan trioleate (Span 85) and sorbitan monolaurate but without limitation thereto. Tween 80 is preferably comprised in an emulsion.

Mixtures of surface active agents such as Tween 80/Span 85 can be used. A combination of polyoxyethylene sorbitan ester such as Tween 80 and octocynol such as Triton X-100 is also suitable. A combination of Laureth 9 and Tween and/or octocynol is also advantageous. Preferably, the amount of polyoxyethylene sorbitan ester (such as Tween 80) included is 0.01% to 1% (w/v), in particular 0.1%; the amount of octylphenoxy polyoxyethanol or nonylphenoxy polyoxyethanol (such as Triton X-100) included is 0.001% to 0.1% (w/v), in particular 0.005% to 0.02%; and the amount of polyoxyethylene ether (such as laureth 9) included is 0.1% to 20% (w/v), possibly 0.1% to 10%, in particular 0.1% to 1% or about 0.5%. In one embodiment, the pharmaceutical composition is delivered via a release control system. For example, intravenous infusion, transdermal patch, liposome, or other routes can be used for administration. In one aspect, macromolecules such as microsphere or implant can be used.

The above disclosure generally describes the present invention. A more complete understanding can be obtained by reference to the following specific examples. These examples are described solely for the purpose of illustration and are not intended to limit the scope of the invention.

EXAMPLES

Example 1

Preparation of *S. pneumoniae* Capsular Polysaccharide

Cultivation of *S. pneumoniae* and purification of capsular polysaccharides were conducted as known to one of ordinary skill in the art. *S. pneumoniae* serotypes were obtained from the American Type Culture Collection (ATCC). *S. pneumoniae* were characterized by capsules and immobility, Gram-positive lancet-shaped diplococcus and alpha hemolysis in a blood agar medium. Serotypes were identified by Quelling test using specific anti-sera (U.S. Pat. No. 5,847,112).

Preparation of Cell Banks

Several generations of seed stocks were created in order to expand the strain and remove components of animal origin (generations F1, F2, and F3). Two additional generations of seed stocks were produced. The first additional generation was made from an F3 vial, and the subsequent generation was made from a vial of the first additional generation. Seed vials were stored frozen (≤−70° C.) with synthetic glycerol as a cryopreservative. For cell bank preparation, all cultures were grown in a soy-based medium. Prior to freezing, cells were concentrated by centrifugation, spent medium was removed, and cell pellets were re-suspended in a fresh medium containing a cryopreservative (such as synthetic glycerol).

Inoculation

Cultures from the working cell bank were used to inoculate seed bottles containing a soy-based medium. The seed bottle was used to inoculate a seed fermentor containing a soy-based medium.

Seed Fermentation

Seed fermentation was conducted in a seed fermentor with the temperature and pH controlled. After the target optical density was reached, the seed fermentor was used to inoculate the production fermentor containing the soy-based medium.

Production Fermentation

Production fermentation is the last step in fermentation. Temperature, pH and agitation speed were controlled.

Inactivation

The fermentation was terminated after cessation of growth by addition of an inactivator. After inactivation, the contents in the fermentor were cooled and the pH of the lysed culture broth was adjusted.

Purification

Broth from the fermentor was centrifuged and filtered to remove bacterial cell debris. Several concentration/diafiltration operations, precipitation/elution, and depth filtration steps were used to remove contaminants and purify capsular polysaccharides.

Example 2

Preparation of S. pneumoniae Capsular Polysaccharide-$CRM_{197}$ Conjugate

Polysaccharides of different serotypes were activated following different pathways and then conjugated to $CRM_{197}$. The activation process comprises reduction of the size of capsular polysaccharides to the target molecular weights, chemical activation and buffer exchange via ultrafiltration. Purified $CRM_{197}$ is conjugated to activated capsular polysaccharides, and the conjugates are purified using ultrafiltration and finally filtered through 0.22 μm filter. The process parameters such as pH, temperature, concentration and time are as follows.

(1) Activation

Step 1

Each serotype polysaccharide was diluted with water for injection, sodium acetate and sodium phosphate to a final concentration in a range of 1.0 to 2.0 mg/mL. For serotype 1, sodium hydroxide (0.05M final base concentration) was added and the solution was incubated at 50° C.±2° C. Then, the solution was cooled to 21 to 25° C. and the hydrolysis was stopped by adding 1M HCl until a target pH of 6.0±0.1 was reached. For serotype 3, HCl (0.01M final acid concentration) was added and the solution was incubated at 50° C.±2° C. Then, the solution was cooled to 21 to 25° C. and the hydrolysis was stopped by adding 1M sodium phosphate until a target pH of 6.0±0.1 was reached. For serotype 4, HCl (0.1 M final acid concentration) was added and the solution was incubated at 45□±2□. Then, the solution was cooled to 21 내지 25° C. and the hydrolysis was stopped by adding 1M sodium phosphate until a target pH of 6.0±0.1 was reached. For serotype 6A, glacial acetic acid (0.2M final acid concentration) was added and the solution was incubated at 60° C.±2° C. Then, the solution was cooled to 21 to 25° C. and the hydrolysis was stopped by adding 1M sodium hydroxide until a target pH of 6.0±0.1 was reached. For serotype 14 and 18C, glacial acetic acid (0.2M final acid concentration) was added and the solution was incubated at 94° C.±2° C. Then, the solution was cooled to 21 to 25° C. and the hydrolysis was stopped by adding 1M sodium phosphate until a target pH of 6.0±0.1 was reached.

Step 2: Periodate Reaction

The required sodium periodate molar equivalents for pneumococcal saccharide activation was determined using total saccharide content. With thorough mixing, the oxidation reaction was allowed to proceed for between 16 to 20 hours at 21-25° C. for all serotypes except 1, 7F, and 19F, for which the temperature was ≤10° C.

Step 3: Ultrafiltration

The oxidized saccharide was concentrated and diafiltered with water for injection (WFI) on a 100 kDa MWCO ultrafilter (30 kDa ultrafilter for serotype 1 and 5 kDa ultrafilter for serotype 18C). Diafiltration was accomplished using 0.9% sodium chloride solution for serotype 1, 0.01 M sodium acetate buffer (pH 4.5) for serotype 7F, and 0.01 M sodium phosphate buffer (pH 6.0) for serotype 19F. The permeate was discarded and the retentate was filtered through a 0.22 μm filter Step 4: Lyophilization For serotypes 3, 4, 5, 9N, 9V, and 14, the concentrated saccharide was mixed with $CRM_{197}$ carrier protein, filled into glass bottles, lyophilized and then stored at −25°±5° C.

For serotypes 2, 6A, 6B, 7F, 19A, 19F, and 23F, a specified amount of sucrose was added which was calculated to achieve a 5%±3% sucrose concentration in the conjugation reaction mixture. Serotypes 1 and 18C did not require sucrose addition. The concentrated saccharide was then filled into glass bottles, lyophilized and then stored at −25°±5° C.

(2) Conjugation Process

Aqueous conjugation was conducted for serotypes 1, 3, 4, 5, 9N, 9V, 14, and 18C, and DMSO conjugation was conducted for serotypes 2, 6A, 6B, 7F, 19A, 19F and 23F.

Step 1: Dissolution

Aqueous Conjugation

For serotypes 3, 4, 5, 9N, 9V and 14, the lyophilized activated saccharide-$CRM_{197}$ mixture was thawed and equilibrated at room temperature. The lyophilized activated saccharide-$CRM_{197}$ was then reconstituted in a 0.1 M sodium phosphate buffer at a typical ratio by serotype. For serotypes 1 and 18C, the lyophilized saccharide was reconstituted in a solution of $CRM_{197}$ in 1 M dibasic sodium phosphate at a typical ratio of 0.11 L of sodium phosphate per 1 L of CRM197 solution.

Dimethyl Sulfoxide (DMSO) Conjugation

The lyophilized activated saccharide serotypes 2, 6A, 6B, 7F, 19A, 19F, 23F and the lyophilized $CRM_{197}$ carrier protein were equilibrated at room temperature and reconstituted in DMSO.

Step 2: Conjugation Reaction

Aqueous Conjugation

For serotypes 1, 3, 4, 5, 9N, 9V, 14 and 18C, the conjugation reaction was initiated by adding the sodium cyanoborohydride solution (100 mg/mL) to achieve 1.0-1.2 moles sodium cyanoborohydride per mole of saccharide. The reaction mixture was incubated for 44-96 hours at 23° C. to 37° C. The temperature and reaction time were adjusted by serotype. The temperature was then reduced to 23°±2° C. and sodium chloride 0.9% was added to the reactor. Sodium borohydride solution (100 mg/mL) was added to achieve 1.8-2.2 molar equivalents of sodium borohydride per mole saccharide. The mixture was incubated for 3-6 hours at 23°±2° C. This procedure reduced any unreacted aldehydes present on the saccharides. The mixture was diluted with sodium chloride 0.9% and the diluted conjugation mixture was filtered using a 1.2 μm pre-filter into a holding vessel.

DMSO Conjugation

For serotypes 2, 6A, 6B, 7F, 19A, 19F and 23F, activated saccharide and $CRM_{197}$ carrier protein were mixed at a ratio range of 0.8 g-1.25 g saccharide/g $CRM_{197}$. The conjugation reaction was initiated by adding the sodium cyanoborohydride solution (100 mg/mL) at a ratio of 0.8-1.2 molar equivalents of sodium cyanoborohydride to one mole activated saccharide. WFI was added to the reaction mixture to a target of 1% (v/v), and the mixture was incubated for 11-27 hours at 23°±2° C. Sodium borohydride solution, 100 mg/mL (typical 1.8-2.2 molar equivalents sodium borohydride per mole activated saccharide) and WFI (target 5% v/v) were added to the reaction and the mixture was incubated for 3-6 hours at 23°±2° C. This procedure reduced any unreacted aldehydes present on the saccharides. Then, the reaction mixture was diluted with sodium chloride 0.9%, and the diluted conjugation mixture was filtered using a 1.2 μm pre-filter into a holding vessel.

Step 3: Ultrafiltration

The diluted conjugate mixture was concentrated and diafiltered on a 100 kDa MWCO ultrafiltration filter with a minimum of 20 volumes of 0.9% sodium chloride or buffer. The permeate was discarded.

Step 4: Sterile Filtration

The retentate after the 100 kDa MWCO diafiltration was filtered through a 0.22 μm filter. In-process controls (saccharide content, free protein, free saccharide, residual DMSO and residual cyanide; for DMSO conjugation, residual DMSO in addition thereto) were performed on the filtered product. In-process controls on filtered retentate were performed to determine whether additional concentration, diafiltration, and/or dilution were needed. As necessary, the filtered conjugate was diluted with 0.9% sodium chloride to achieve a final concentration of less than 0.55 g/L. Release tests for saccharide content, protein content and saccharide:protein ratio were performed at this stage. Finally, the conjugate was filtered (0.22 μm) and release test (appearance, free protein, free saccharide, endotoxin, molecular size determination, residual cyanide, residual DMSO, saccharide identity and CRM197 identity) was performed. The final bulk concentrated solution was stored at 2-8□.

Example 3

Formulation of a Multivalent Pneumococcal Conjugate Vaccine

The required volumes of final bulk concentrates were calculated based on the batch volume and the bulk saccharide concentrations. After the required amounts of the 0.85% sodium chloride (physiological saline), polysorbate 80 and succinate buffer were added to the pre-labeled formulation vessel, bulk concentrates were added. The preparation was then thoroughly mixed and sterile filtered through a 0.22 μm membrane. The formulated bulk was mixed gently during and following the addition of bulk aluminum phosphate. The pH was checked and adjusted if necessary. The formulated bulk product was stored at 2-8□. The product contained, in a 0.5 ml volume, 2 μg of each saccharide, except for 6B at 4 μg; approximately 34 μg CRM197 carrier protein; 0.125 mg of elemental aluminum (0.5 mg aluminum phosphate) adjuvant; 4.25 mg of sodium chloride; 295 μg of sodium succinate buffer; and 100 μg of polysorbate 80.

Example 4

Immunogenicity of the Multivalent Pneumococcal Conjugate Vaccine

The multivalent pneumococcal vaccine, i.e., the vaccine composition (SK-15) prepared in Example 3 was tested for its ability to induce an immunogenic response in rabbits. These immunogenic effects were characterized by antigen-specific ELISA for serum IgG concentrations and by opsonophagocytic assay (OPA) for antibody function. New Zealand White rabbits were immunized intramuscularly at week 0 and week 3 with the planned human clinical dose of each polysaccharide (2 μg of each PS, except for 6B at 4 ug). Sera were sampled every 3 weeks post immunization.

Measurement of Serotype Specific IgG Concentration

Figure 2:
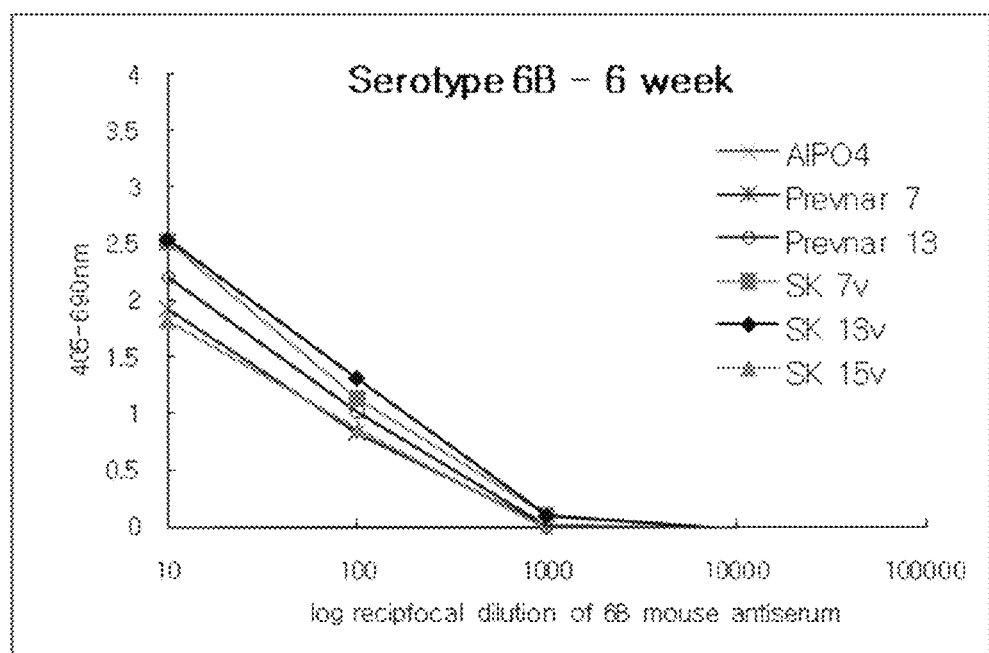
Figure 3:
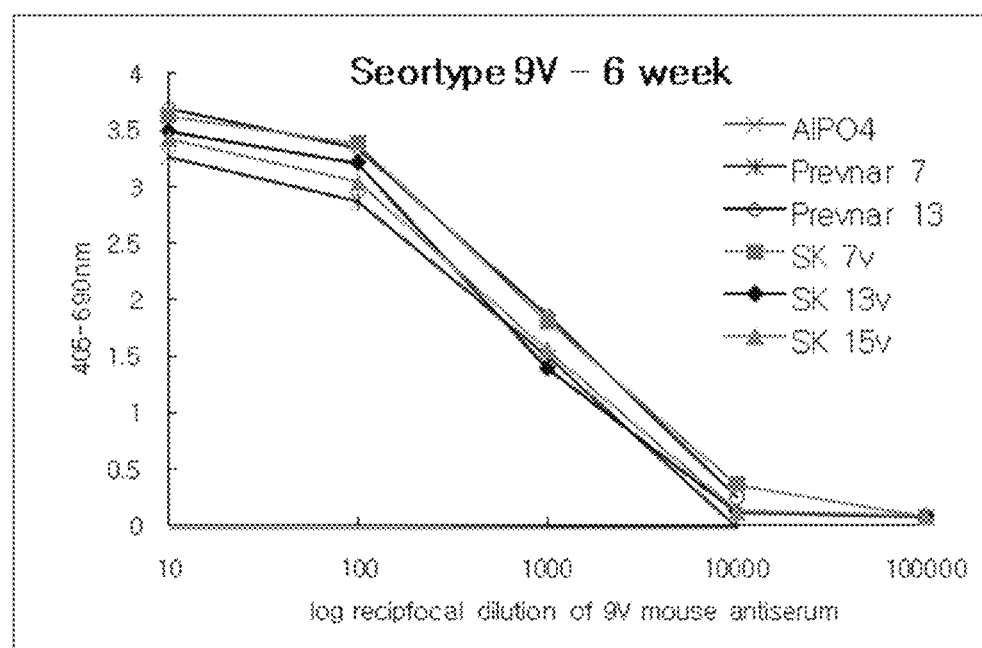
Figure 4:
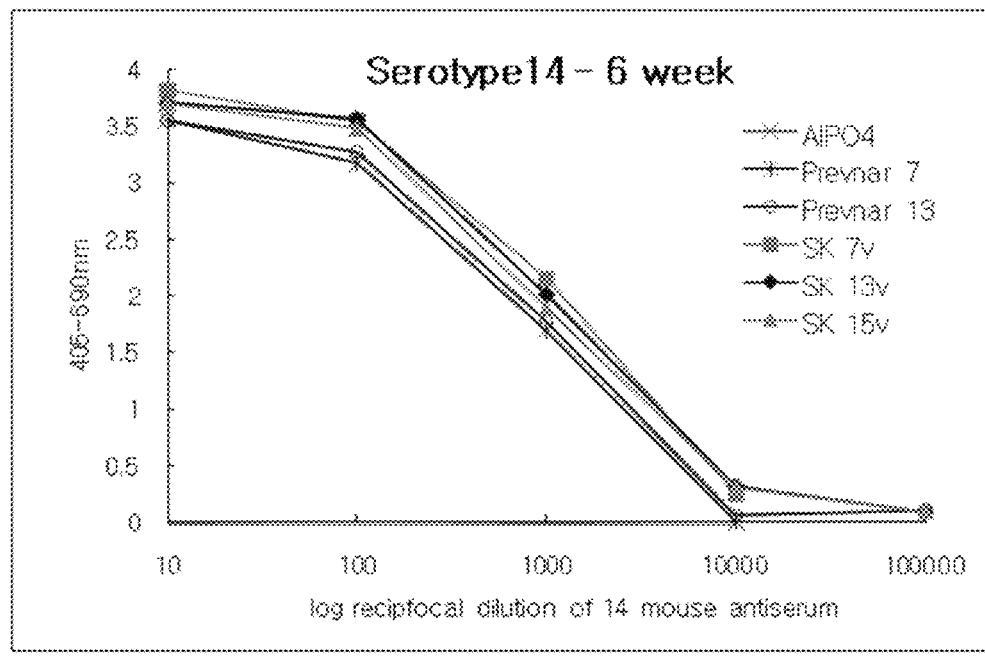
Figure 5:
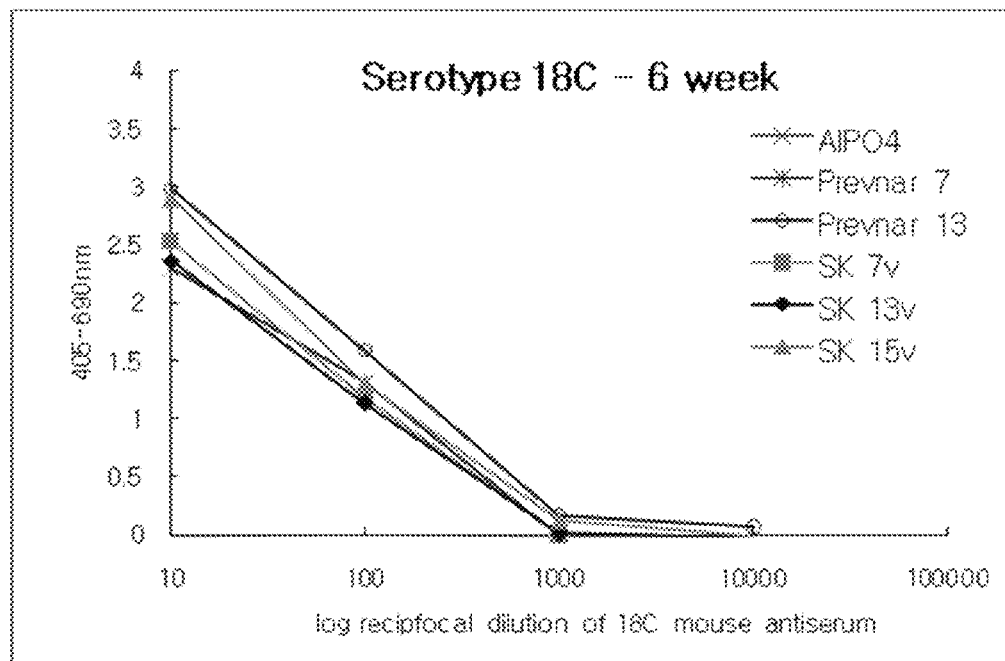
Figure 6:
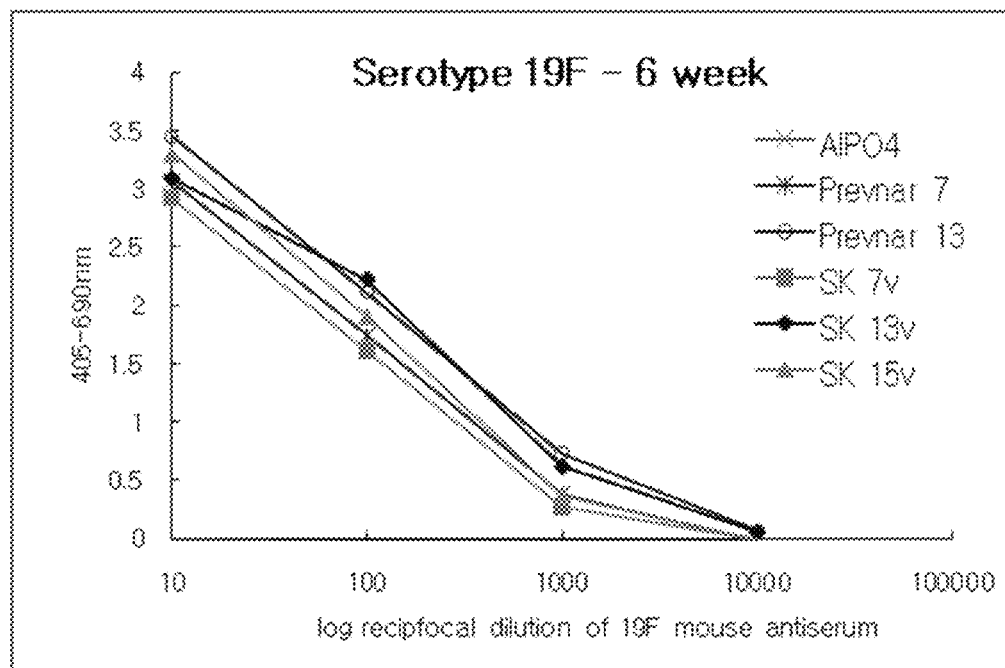
Figure 7:
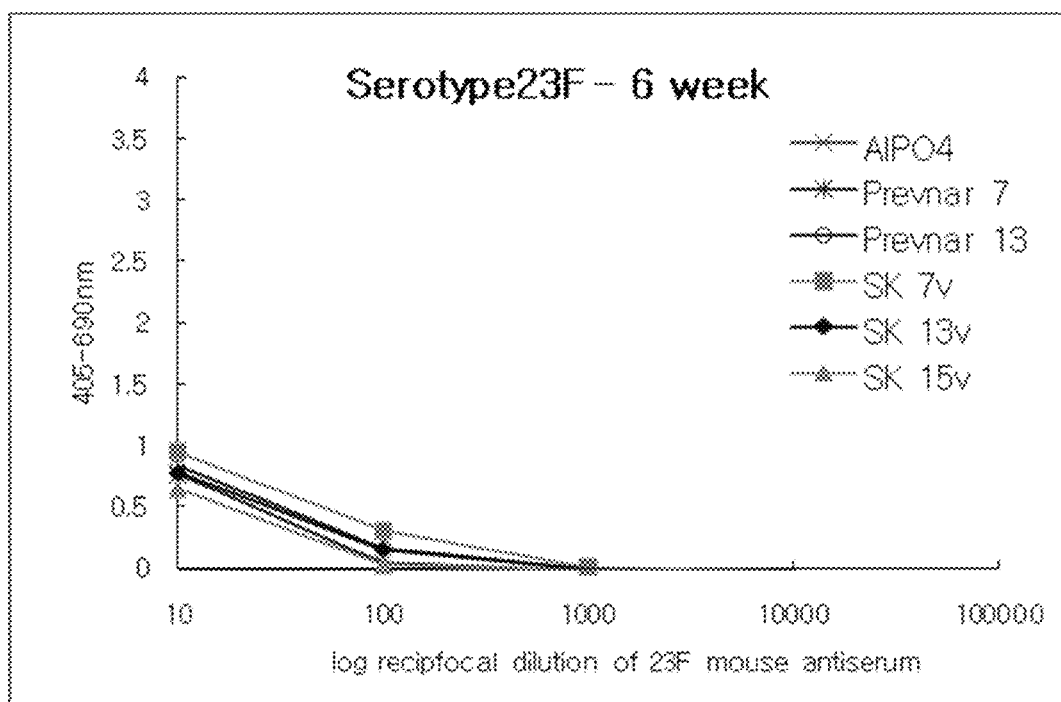
Figure 8:
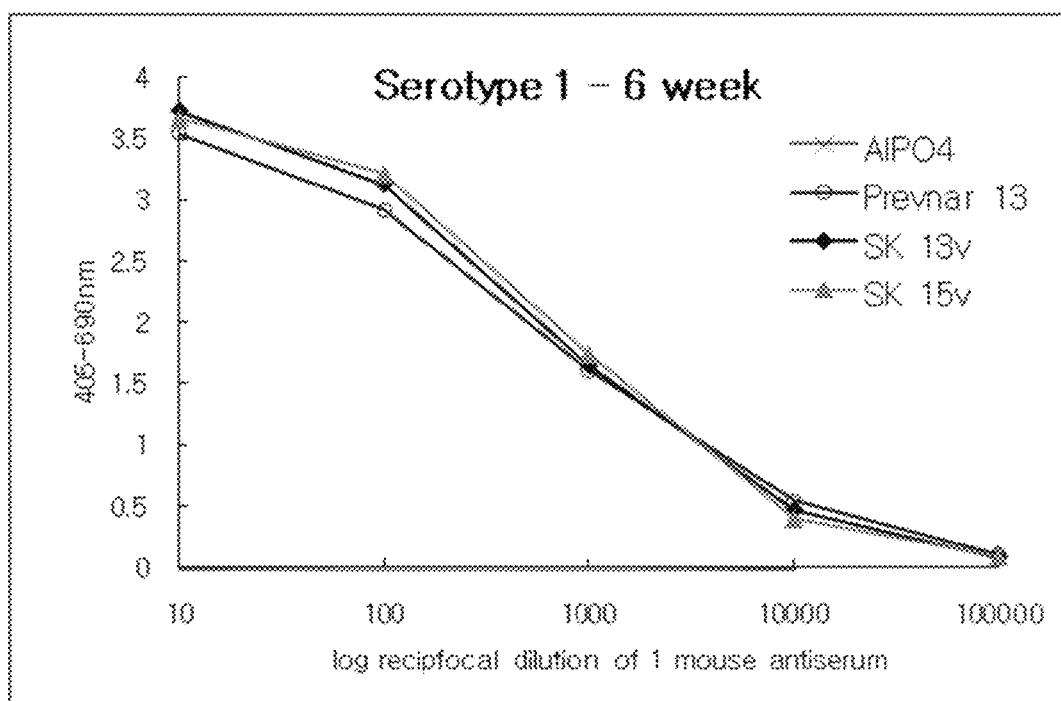
Figure 9:
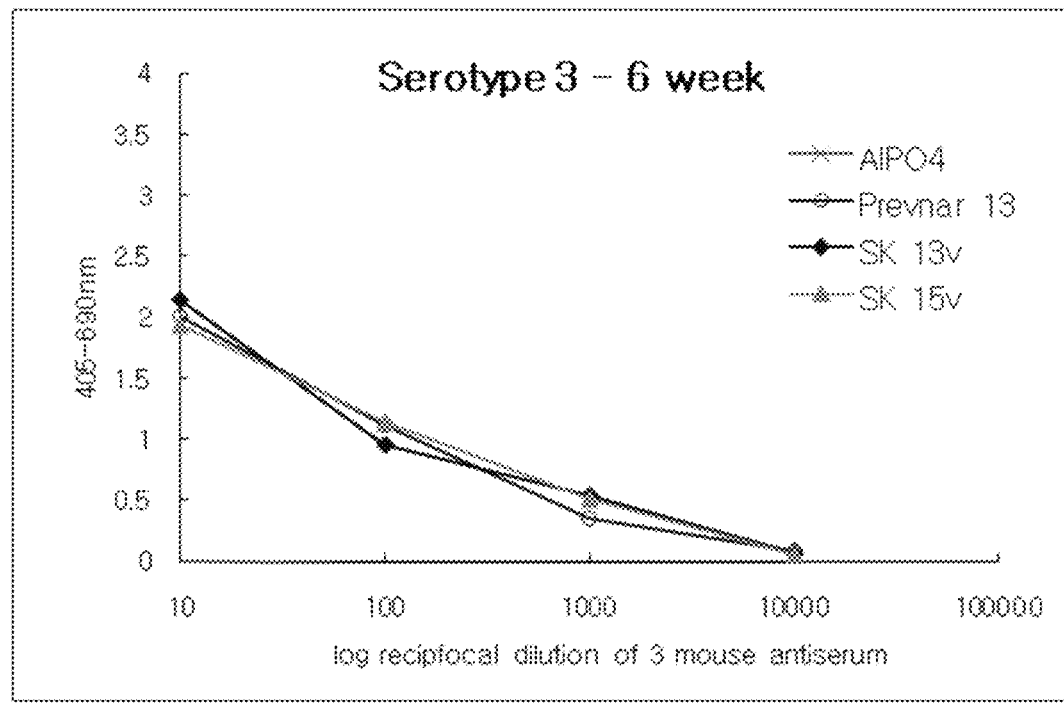
Figure 10:
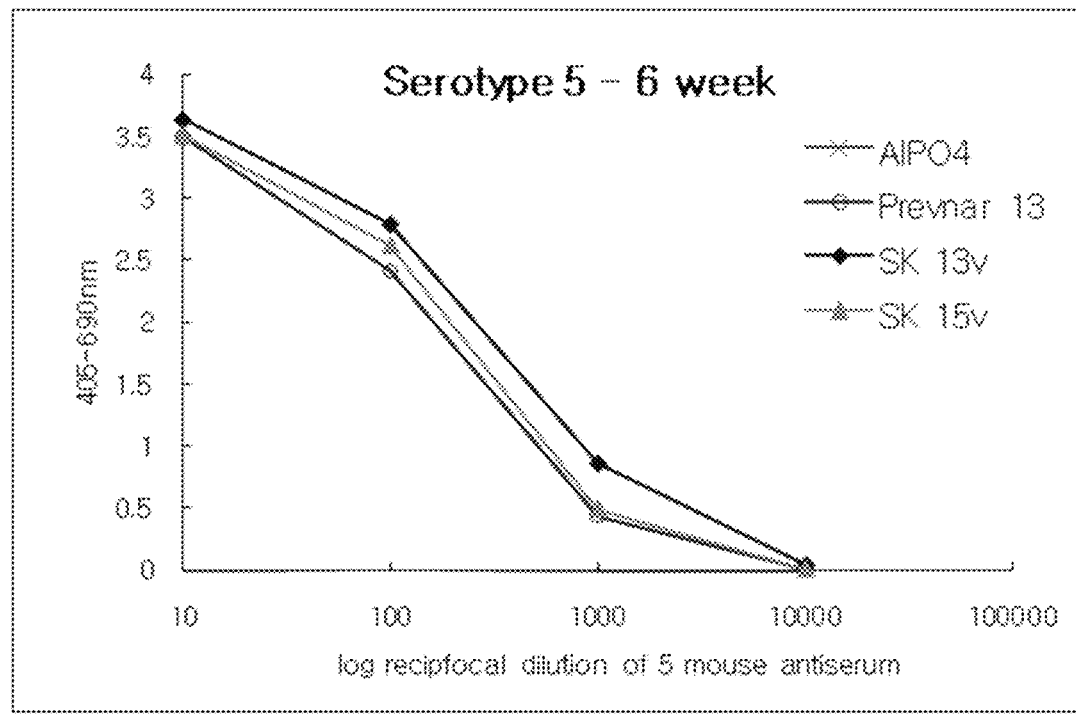
Figure 11:
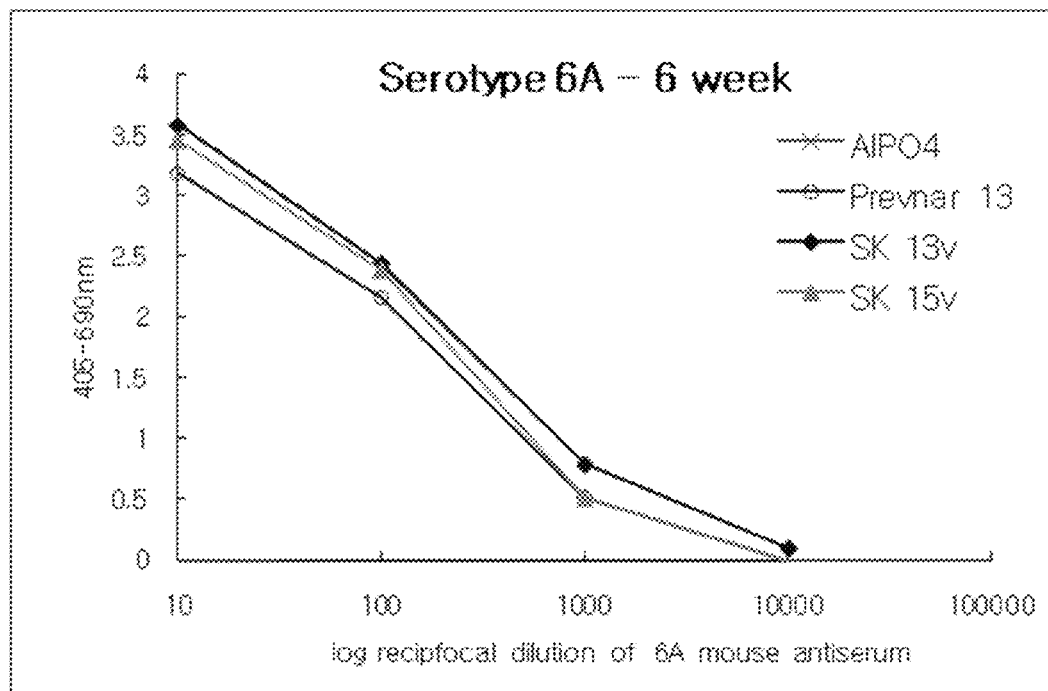
Figure 12:
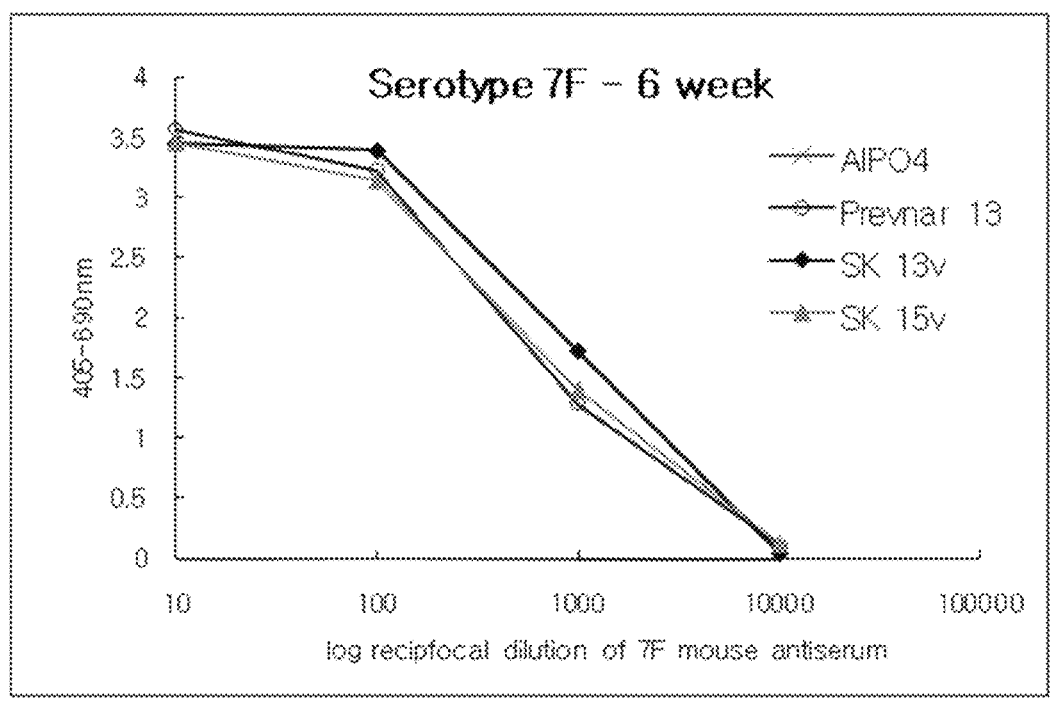
Figure 13:
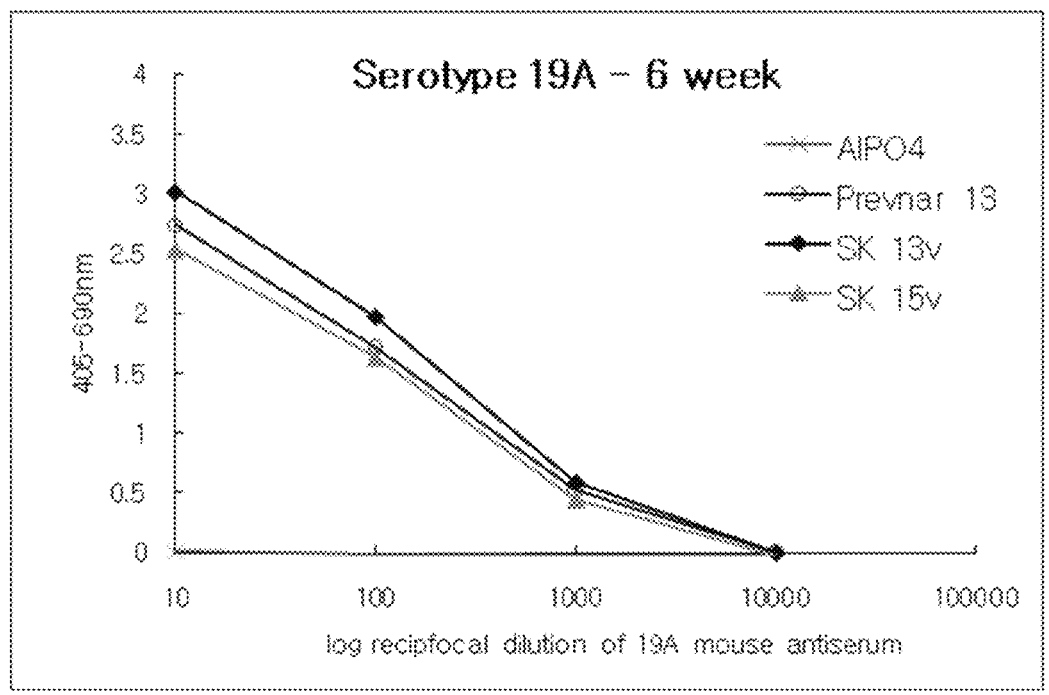
Figure 14:
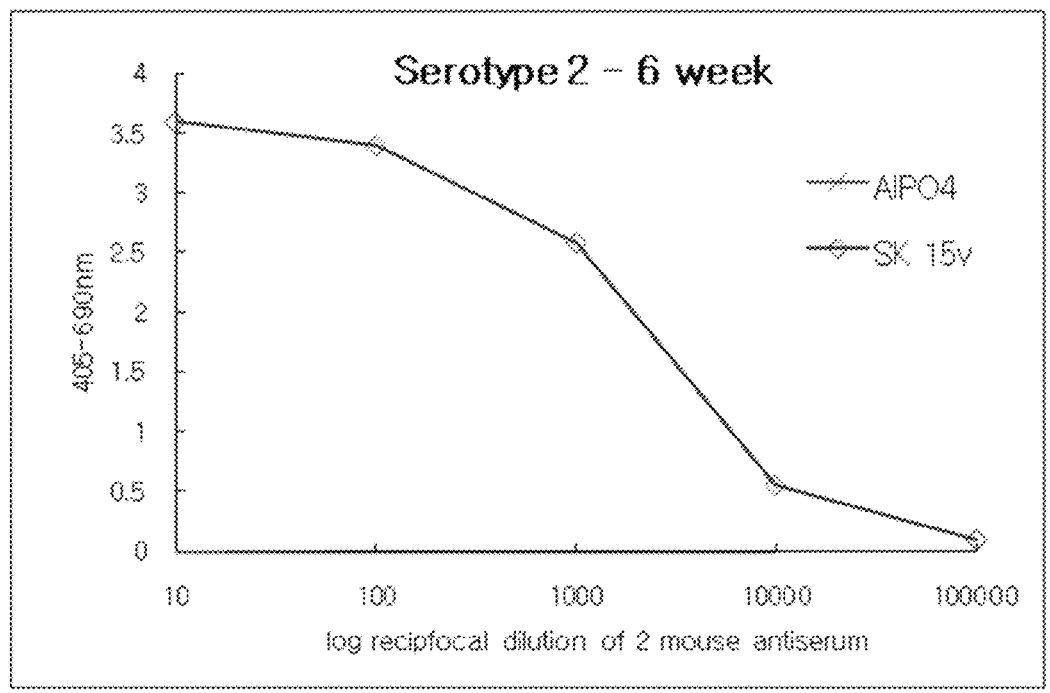
Figure 15:
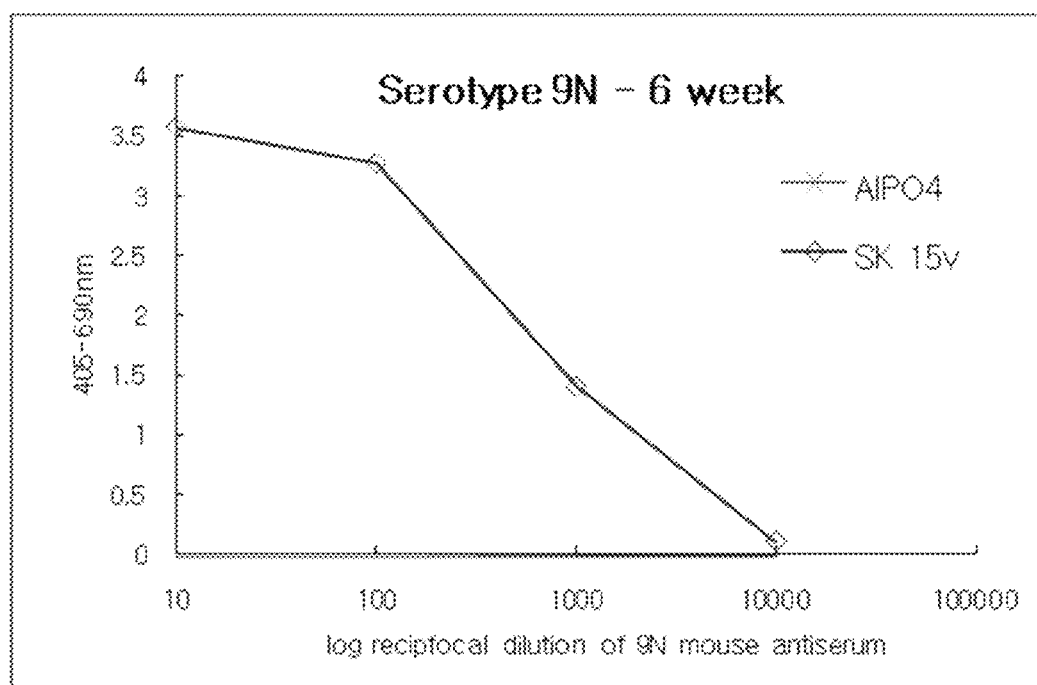

Capsular polysaccharides (PnPs) for each serotype were coated on a 96-well plate at 500 ng/well. An equivalent amount of serum was sampled from each subject and was pooled by group. The serum pool was serially diluted by 10 times with an antibody dilution buffer comprising Tween 20, C-PS 4 ug/mL and serotype 22F capsular polysaccharide (PnPs 22F) 4 ug/mL and then reacted at room temperature for 30 minutes. The plate was washed 5 times with a washing buffer and then the well plate was coated with pre-adsorbed and diluted serum 50 uL and was incubated at room temperature for 18 hours. The well plate was washed in the same way and then goat anti-Rabbit IgG-alkaline phosphatase conjugates (1:50000) were added to each well, followed by incubation at room temperature for 2 hours. Plates were washed as described above and 1 mg/mL p-nitrophenylamine buffer as substrate was added to each well and then reacted at room temperature for 2 hours. The reaction was quenched by adding 50 uL of 3M NaOH and absorbances at 405 nm and 690 nm were measured. As comparative examples, 7-valent vaccine (Prevnar 7, Pfizer) and 13-valent vaccine (Prevnar 13, Pfizer) were subjected to the same procedure. The results are shown in FIGS. 1-15.

Functional Immunogenicity Test (OPA)

Antibody functions were evaluated by testing serum in OPA assay. An equivalent amount of serum was sampled from each subject, pooled by group and diluted by 10 times. S. pneumonia was cultured in a THY medium by serotype and diluted to 1000 CFU/10 uL. Opsonization buffer 200 uL, diluted serum 10 uL, and diluted S. pneumonia 10 uL were mixed and reacted at room temperature for 1 hour. A mixture of pre-differentiated HL-60 cells and complements was added and reacted in a $CO_2$ incubater (37□) for one hour. The temperature was reduced to stop phagocytosis and the reaction 5 uL was smeared onto an agar plate pre-dried for 30-60 minutes. The plate was incubated in a $CO_2$ incubater (37□) for 12-18 hours and then colonies were counted. OPA titer was expressed as a dilution rate at which 50% killings were observed. As a comparative example, 13-valent vaccine (Prevnar 13, Pfizer) was subjected to the same procedure. The results are shown in Tables 1-3.

TABLE 1

OPA Titers of 15 polysaccharide serotypes 3 weeks after primary immunization

| Serotype | Prevnar 13 | SK-15 | Serotype | Prevnar 13 | SK-15 |
|---|---|---|---|---|---|
| 1 | 1:16 | 1:4 | 9V | 1:256 | 1:256 |
| 2 | — | 1:128 | 9N | — | 1:512 |
| 3 | No dilution | No dilution | 14 | 1:256 | 1:256 |
| 4 | 1:128 | 1:128 | 18C | 1:1024 | 1:1024 |
| 5 | 1:64 | 1:32 | 19A | 1:512 | 1:256 |
| 6A | 1:512 | 1:256 | 19F | 1:256 | 1:128 |
| 6B | 1:256 | 1:128 | 23F | 1:256 | 1:256 |
| 7F | 1:1024 | 1:1024 | — | — | — |

TABLE 2

OPA Titers of 15 polysaccharide serotypes 3 weeks after second immunization

| Serotype | Prevnar13 | SK-15 | Serotype | Prevnar 13 | SK-15 |
|---|---|---|---|---|---|
| 1 | 1:64 | 1:64 | 9V | 1:512 | 1:512 |
| 2 | — | 1:512 | 9N | — | 1:2048 |
| 3 | 1:2 | 1:4 | 14 | 1:1024 | 1:1024 |
| 4 | 1:1024 | 1:1024 | 18C | 1:1024 | 1:512 |
| 5 | 1:256 | 1:256 | 19A | 1:1024 | 1:1024 |
| 6A | 1:2048 | 1:2048 | 19F | 1:1024 | 1:512 |
| 6B | 1:2048 | 1:2048 | 23F | 1:2048 | 1:2048 |
| 7F | 1:2048 | 1:2048 | — | — | — |

TABLE 3

OPA Titers of 15 polysaccharide serotypes 6 weeks after second immunization

| Serotype | Prevnar 13 | SK-15 | Serotype | Prevnar 13 | SK-15 |
|---|---|---|---|---|---|
| 1 | 1:64 | 1:64 | 9V | 1:512 | 1:512 |
| 2 | — | 1:512 | 9N | — | 1:2048 |
| 3 | 1:4 | 1:4 | 14 | 1:1024 | 1:1024 |
| 4 | 1:1024 | 1:1024 | 18C | 1:2048 | 1:2048 |
| 5 | 1:512 | 1:512 | 19A | 1:2048 | 1:1024 |
| 6A | 1:2048 | 1:2048 | 19F | 1:1024 | 1:512 |
| 6B | 1:2048 | 1:1024 | 23F | 1:2048 | 1:2048 |
| 7F | 1:2048 | 1:2048 | — | — | — |

Serotype-specific immune response by the vaccine formulation of the present invention and that of the comparative example were evaluated via IgG ELISA and complement-mediated OPA for functional antibody. FIGS. 1 to 15 show the results of IgG ELISA and Tables 1 to 3 show the results of functional immunogenicity measurements obtained by OPA, comparing the immune responses among treatment groups. These results indicate that the 15-valent pneumococcal polysaccharide conjugate vaccine would induce IgG titer and functional antibody activity equivalent to or better than Prevnar-13.

The invention claimed is:

1. A multivalent immunogenic composition consisting of 15 distinct capsular polysaccharide-protein conjugates, together with at least one of a physiologically acceptable vehicle and an adjuvant, wherein the capsular polysaccharides are prepared from *Streptococcus pneumoniae* serotypes 1, 2, 3, 4, 5, 6A, 6B, 7F, 9N, 9V, 14, 18C, 19A, 19F and 23F, and wherein the carrier protein is $CRM_{197}$.

2. The multivalent immunogenic composition of claim 1, wherein the adjuvant is an aluminum-based adjuvant.

3. The multivalent immunogenic composition of claim 2, wherein the adjuvant is selected from the group consisting of aluminum phosphate, aluminum sulfate and aluminum hydroxide.

4. The multivalent immunogenic composition of claim 3, wherein the adjuvant is aluminum phosphate.

5. The multivalent immunogenic composition of claim 1, which is for inducing an immune response to a *Streptococcus pneumoniae* capsular polysaccharide conjugate.

6. The multivalent immunogenic composition of claim 5, wherein the multivalent immunogenic composition is a single 0.5 ml dose formulated to contain:
   2 µg of each saccharide, except for 6B at 4 µg;
   Approximately 34 µg of the $CRM_{197}$ carrier protein;
   0.125 mg of elemental aluminum (0.5 mg aluminum phosphate) adjuvant; and
   sodium chloride and sodium succinate buffer as excipients.

7. The multivalent immunogenic composition of claim 2, which is for inducing an immune response to a *Streptococcus pneumoniae* capsular polysaccharide conjugate.

8. The multivalent immunogenic composition of claim 7, wherein the multivalent immunogenic composition is a single 0.5 ml dose formulated to contain:
   2 µg of each saccharide, except for 6B at 4 µg;
   approximately 34 µg of the $CRM_{197}$ carrier protein;
   0.125 mg of elemental aluminum (0.5 mg aluminum phosphate) adjuvant; and
   sodium chloride and sodium succinate buffer as excipients.

9. The multivalent immunogenic composition of claim 3, which is for inducing an immune response to a *Streptococcus pneumoniae* capsular polysaccharide conjugate.

10. The multivalent immunogenic composition of claim 9, wherein the multivalent immunogenic composition is a single 0.5 ml dose formulated to contain:
    2 µg of each saccharide, except for 6B at 4 µg;
    approximately 34 µg of the $CRM_{197}$ carrier protein;
    0.125 mg of elemental aluminum (0.5 mg aluminum phosphate) adjuvant; and
    sodium chloride and sodium succinate buffer as excipients.

11. The multivalent immunogenic composition of claim 4, which is for inducing an immune response to a *Streptococcus pneumoniae* capsular polysaccharide conjugate.

12. The multivalent immunogenic composition of claim 11, wherein the multivalent immunogenic composition is a single 0.5 ml dose formulated to contain:
    2 µg of each saccharide, except for 6B at 4 µg;
    approximately 34 µg of the $CRM_{197}$ carrier protein;
    0.125 mg of elemental aluminum (0.5 mg aluminum phosphate) adjuvant; and
    sodium chloride and sodium succinate buffer as excipients.

* * * * *